United States Patent [19]

Lindskog et al.

[11] Patent Number: 5,188,835
[45] Date of Patent: Feb. 23, 1993

[54] INTRAVAGINAL DEVICES

[75] Inventors: Inga M. Lindskog, Helsingborg; Bengt C. H. Sjögren, Viken; Sven-Börje Andersson, ÖdÅkra, all of Sweden

[73] Assignee: Kabi Pharmacia AB, Uppsala, Sweden

[21] Appl. No.: 793,484

[22] Filed: Nov. 12, 1991

Related U.S. Application Data

[63] Continuation of Ser. No. 337,074, Apr. 12, 1989, abandoned, which is a continuation of Ser. No. 60,833, Jun. 12, 1987, Pat. No. 4,871,543.

[30] Foreign Application Priority Data

Jun. 16, 1986 [SE] Sweden .............................. 8602666-3

[51] Int. Cl.$^5$ ................................................ A61F 6/14
[52] U.S. Cl. ................................... 424/432; 424/430; 128/832
[58] Field of Search ................. 424/432, 430; 128/832

[56] References Cited

U.S. PATENT DOCUMENTS

| | | | |
|---|---|---|---|
| 3,586,710 | 6/1971 | Los .................. | 514/874 X |
| 3,733,407 | 5/1973 | Segre ................. | 514/874 X |
| 3,761,497 | 9/1973 | Serebryakova ................. | 260/397.5 |
| 3,895,103 | 7/1975 | Zaffaroni .............. | 424/432 |
| 4,155,991 | 5/1979 | Schopflin ............. | 424/432 |
| 4,250,611 | 2/1981 | Wong ................. | 128/832 |
| 4,259,325 | 3/1981 | Prezewowsky et al. ....... | 514/874 X |
| 4,292,965 | 10/1981 | Nash ................. | 128/260 |
| 4,402,695 | 9/1983 | Wong ................. | 604/892 |
| 4,526,578 | 7/1985 | Wong ................. | 604/892 |
| 4,553,972 | 11/1985 | Vickery ................. | 604/892 |
| 4,596,576 | 6/1986 | De Nijs ................. | 604/892 |
| 4,871,543 | 10/1989 | Lindskog ................. | 424/430 |

FOREIGN PATENT DOCUMENTS

| | | |
|---|---|---|
| 450107 | 9/1976 | Fed. Rep. of Germany . |
| 53-065865 | 6/1978 | Japan ................. 12/308 |

OTHER PUBLICATIONS

Maturitas vol. 3, 1981 pp. 125-133 Pharmacokinetics and pharmacodynamic effects of vaginal oestradiol administration from silastic rings in post-menopausal women.

Journ. Clinical Endocrinology vol. 54, No. 1, 1982, pp. 208-210 Development of a vaginal ring for achieving physioogic levels of 17 beta-estradiol in hypoestrogenic women.

Obstetrics & Gynecology, vol. 67, No. 1, 1986, pp. 91-94 (Stumpf) Selecting constant serum estradiol levels achieved by vaginal rings.

*Primary Examiner*—Thurman K. Page
*Assistant Examiner*—William E. Benston
*Attorney, Agent, or Firm*—Fred Philpitt

[57] ABSTRACT

The invention concerns an intravaginal device comprising a combination of 17β-estradiol and a supporting matrix for treating hypoestrogenic women. The device releases continously 17β-estradiol at a rate of about 0.5 to about 25 μg/24 h. The invention also comprises a method of preparing the device and a method of treating hypoestrogenic women by using the device.

6 Claims, No Drawings

INTRAVAGINAL DEVICES

This application is a continuation of application Ser. No. 07/337,074, filed Apr. 12, 1989, now abandoned which is a continuation of application Ser. No. 060,833, filed Jun. 12, 1987, now U.S. Pat. No. 9,871,593.

The present invention concerns intravaginal devices. Especially the invention concerns intravaginal devices releasing a low amount of 17$\beta$-estradiol for a prolonged period of time without undesirable side effects for treating hypoestrogenic women.

BACKGROUND

17$\beta$-estradiol is often used for treating estrogen deficiency. This deficiency origins from e.g. oophorectomy, menopause, radiationinduced ovarian failure, panhypopituitarism and Kallman's syndrome.

When taken orally 17$\beta$-estradiol is relatively ineffective (1,2). Besides, oral estrogens effect the liver proteins due to portal absorption (3), the intestinal metabolism (4,5) and "bolus" surges of circulating estrogen after each dose (5).

The problem with oral estrogen therapy can be avoided by vaginal administration and steroids are well absorbed from vagina. The administration of 17$\beta$-estradiol via intravaginal devices has been suggested and thoroughly studied (6,7,8,9). One of these studies, viz. the study by Englund et al (7), discloses intravaginal devices having an in vitro release rate of 200 $\mu$g/24 h, which corresponded to plasma levels in the women varying between 80–200 pg/ml. In the end of the article it is concluded that the release rate of 200 $\mu$g per day is too high for replacement therapy in postmenopausal women as they exceed the estrogen levels seen in the follicular phase in fertile women. It is suggested that devices releasing 50–100 $\mu$g of 17$\beta$-estradiol per day might deliver the proper dosage.

In the articles by Stumpf (6,9) and Veldhuls (8) the release rates per day are not discussed but the plasma levels disclosed are in the range of 50–150 pg/ml, which is about the same magnitude as disclosed in the Englund article.

THE PRESENT INVENTION

Contrary to what has been studied and suggested it has now been found that intravaginal devices releasing a considerably lower amount of 17$\beta$-estradiol is sufficient to alleviate or eliminate symptoms depending on estrogen-deficiency. These symptoms may be e.g. feelings of vaginal dryness, pruritus, dyspareunia, smarting pain at micturition, urinary urgency and frequency. It has also been found that when the low dosage according to the present invention is used a drastical decrease of undesired side effects such as spotting, break-through and withdrawal bleeding is obtained.

The intravaginal devices according to the present invention are characterized in that they continuously release 17$\beta$-estradiol at a rate of about 0.5 to 25 $\mu$g/24 h.

The invention also concerns a method of treating hypoestrogenic women by retainably positioning within a woman a medicated intravaginal device, which continuously releases 17$\beta$-estradiol at a rate of about 0.5 to about 25 $\mu$g/24 h.

Preferably the release rate varies between 1 and 10 $\mu$g/24 h, the most suitable release rate varying between 4 and 8 $\mu$g/24 h.

The period of continuous and essentially constant release of estradiol from the device according to the invention can include essentially any period varying from a day to year and this period will depend on several factors. A usual period is 3 or 4 months. Preferably the release rate is essentially constant for at least a month.

The device according to the invention can have any shape adapted for intravaginal administration. A preferred type of device is the intravaginal ring.

In the field of intravaginal rings (IVR) there are basically five different designs. The first design concerns an IVR, wherein the steroid is homogenously dispersed throughout an inert elastomer as described in the U.S. Pat. No. 3,545,397.

The second IVR consists of an inert elastomer ring encircled by a second ring of inert elastomer impregnated with a steroid (cf.e.g. the U.S. Pat. No. 4,012,496).

In a third type of IVR (the Roseman IVR) a thin layer of an inert elastomer containing a steroid is moulded onto a central inert core of elastomer.

In the fourth type a thin medicated layer of an inert elastomer containing a steroid surrounds a central inert core of synthetic elastomer and the medicated layer is surrounded by an outer layer of inert elastomer of variable thickness. This type of ring is disclosed in the U.S. Pat. No. 4,292,965.

A fifth type of IVR consists of a central core of elastomer that is admixed with a steroid surrounded by an outer layer of inert elastomer. This type is described in CONTRACEPTION, Vol. 17, No. 3, pages 221–230, March 1978. The disclosures of these references are incorporated herein by reference.

The invention also includes a method of preparing an intravaginal device for treating hypoestrogenic women. The method comprises the steps of combining 17$\beta$-estradiol and a supporting matrix, whereby the relative amounts of 17$\beta$-estradiol and matrix are selected in such a way that the device will continously release 17$\beta$-estradiol at a rate between about 0.5 and 25 $\mu$g/24 h. Preferably the release rate varies from about 1 to about 10 $\mu$g/24 h, and most preferably from about 4 to about 8 $\mu$g/24 h.

The elastomer of the matrix can be chosen from a wide variety of materials known in the art and the release rate of the estradiol is governed by Fick's law. The elastomers can e.g. be chosen from hydroxyl-terminated organopolysiloxanes of the RTV (room temperature vulcanizing) type which harden to elastomers at room temperature after the addition of cross-linking agents in the presence of curing catalysts and under the atmospheric humidity. Typical curing catalysts are metallic salts of carboxylic acids, preferably tin salts, e.g. tin (II) octoate and tin (II)-2-ethylhexanoate. Other suitable elastomers are two-component dimethylpolysiloxane compositions, which are platinum-catalyzed at room temperature or under slightly elevated temperature and capable of addition cross-linking.

According to a preferred embodiment the device has the form of a ring that may be prepared by homogenously suspending 17$\beta$-estradiol in a pharmacologically acceptable elastomer; preparing a core from said elastomer; mounting an outer layer of a pharmaceutically acceptable elastomer around the core and curing the device obtained.

It is obvious that the curing temperature and the curing time can vary within broad ranges and depend i.a. on the elastomer used. The core and the surrounding unmedicated layer can be made of the same elastomer.

The curing temperature may vary between room temperature and 150° C. and is preferably 40°-90° C. The curing time may vary between a few seconds to several days. In practice, however, curing times less than one hour are preferred.

In order to obtain the release rates according to the invention the ratio between the core diameter and the thickness of the tubing should preferably vary between 0.3 and 6, and most preferably between 0.4 and 2.

EXAMPLES

The invention is further illustrated by the following examples.

EXAMPLE 1

One part of pure micronized 17β-estradiol was mixed with 250 parts of fluid polydimethylsiloxane (382 Silastic ® Medical Grade Elastomer). The mixture was activated by stannous octoate and injected under pressure into two piece ring molds, each having an outside diameter of 543 mm and an inside diameter of 539 mm. The mixture in the molds was polymerized and the solid rings having a cross-sectional diameter of 2 mm were then removed. Silicone (382 Silastic ® Medical Grade Elastomer) tubing having a thickness of 3.5 mm was molded around the rings, thus resulting in a first set of intravaginal rings consisting of a medicated inner 2 mm core and an unmedicated outer 3.5 mm layer. These rings released approximately 8 μg/24 h of estradiol for a period of 150 days. The content of estradiol was 1.91 mg/ring and of Silastic ® 11 g.

EXAMPLE 2

A second set of intravaginal rings was similarly produced and released approximately 20 μg/24 h of estradiol for a period of 150 days, the difference in such rings being that an unmedicated outer, 1.5 mm thick layer of silicone tubing and a core having a diameter of 6 mm were used. The release rate during the 150 days period of time was fairly constant, but the rate does tend to decrease slightly with time. The content of estradiol was 4.79 mg/ring and of Silastic ® 11 g.

The release rates referred to herein are in vitro release rates, which may be measured according to the procedure set on page 225 of the March 1978 issue of CONTRACEPTION (Vol. 17, No. 3) or the October 1981 issue of CONTRACEPTION (Vol. 24, No. 4) or by any other comparable method.

Thus, one may produce intravaginal devices containing 17β-estradiol in any of a number of different ways, having any of a number of different forms or shapes.

The above release rate testing procedure can be used to determine whether such devices meet the release rate requirements of this invention.

Whereas the foregoing examples involve an admixture of 17β-estradiol and an elastomer, we also contemplate that the 17β-estradiol could be in a carrier liquid, emulsion, gel or oil within a surrounding elastomeric shell that is porous enough to permit controlled release of the 17β-estradiol.

The rings releasing about 8 μg/24 h were tested on 9 post-menopausal women and the rings releasing about 20 μg/24 h were tested on 11 post-menopausal women for a period of three months. The rings were well accepted and the post-menopausal symptoms disappeared in both groups.

No side effects were observed in the women obtaining the estradiol at the rate of 8 μg/24 h. A negligible bleeding was observed in one woman receiving the dose 20 μg/24 h.

Table 1 discloses the in vitro release rate of 17β-estradiol from the two types of rings prepared according to the Examiner.

The tables 2 and 3 indicate the in vivo release rates as well as the correlation between in vitro and in vivo release rate.

TABLE 1

Release of $E_2$ from IVR in vitro (0.9% saline).
Mean values of 3 rings.

| Time, days | Released $E_2$, ug/24 h | |
|---|---|---|
| | A | B |
| 5 | 24 | 9 |
| 10 | 23 | 9 |
| 15 | 23 | 9 |
| 20 | 22 | 9 |
| 25 | 21 | 8 |
| 30 | 21 | 8 |
| 35 | 20 | 8 |
| 40 | 20 | 8 |
| 45 | 20 | 8 |
| 50 | 20 | 8 |
| 60 | 19 | 7 |
| 70 | 18 | 7 |
| 80 | 18 | 7 |
| 90 | 17 | 7 |
| 100 | 16 | 7 |
| 110 | 15 | 7 |
| 120 | 14 | 7 |
| 140 | 14 | 7 |

A = rings containing 4.79 mg estradiol
B = rings containing 1.91 mg estradiol
Release graphs, E2-release versus time, were constructed and the following mean release values were calculated:
Rings Type A - 20.3 μg E2/24 h when used for 97 or 98 days. - 20.6 μg E2/24 h when used for 92 days. - 20.0 μg E2/24 h when used for 105 days.
Rings Type B - 7.8 μg E2/24 h when used for 93 to 99 days.

TABLE 2

Release of $E_2$ in vivo. Analyses of rings type A after use.
Content of $E_2$ before clinical trial: 4.79 mg/ring
(mean value of 13 analyzed rings
Analyses after clinical trial:

| Patient | a | b | c | d | e | f | g | h | i | j | k | Mean |
|---|---|---|---|---|---|---|---|---|---|---|---|---|
| Time of usage, days | 98 | 97 | 97 | 97 | 98 | 98 | 92 | 98 | 98 | 98 | 105 | |
| Content of $E_2$ after use, mg | 2.66 | 3.00 | 3.29 | 2.86 | 2.66 | 2.51 | 2.87 | 2.86 | 2.80 | 2.74 | 2.71 | |
| $E_2$ released, mg | 2.13 | 1.79 | 1.50 | 1.93 | 2.13 | 2.28 | 1.92 | 1.93 | 1.99 | 2.05 | 2.08 | |
| Mean dosage, μg/day | 21.7 | 18.5 | 15.5 | 19.9 | 21.7 | 23.3 | 20.9 | 19.7 | 20.3 | 20.9 | 19.8 | 20.2 |
| Ratio in vivo/in vitro | 1.07 | 0.91 | 0.76 | 0.98 | 1.07 | 1.15 | 1.01 | 0.97 | 1.00 | 1.03 | 1.04 | 1.00 |

TABLE 3

Release of E₂ in vivo. Analyses of rings type B after use.
Content of E₂ before clinical trial: 1.91 mg/ring
(mean value of 10 analyzed rings /1.84–2.00/)

| Patient | l | m | n | o | p | q | r | s | t | Mean |
|---|---|---|---|---|---|---|---|---|---|---|
| Time of usage, days | 98 | 98 | 98 | 98 | 98 | 93 | 99 | 98 | 98 | |
| Content of E₂ after use | 1.18 | 1.21 | 1.35 | 1.17 | 1.31 | 1.41 | 1.13 | 1.32 | 1.18 | |
| E₂ released, mg | 0.73 | 0.70 | 0.56 | 0.74 | 0.60 | 0.50 | 0.78 | 0.59 | 0.73 | |
| Mean dosage, ug/day | 7.4 | 7.1 | 5.7 | 7.6 | 6.1 | 5.4 | 7.9 | 6.0 | 7.4 | 6.6 |
| Ratio in vivo/in vitro | 0.95 | 0.91 | 0.73 | 0.97 | 0.78 | 0.69 | 1.01 | 0.77 | 0.95 | 0.84 |

REFERENCES

1. Botella-Llusia J 1973 Endocrinology of Women, W.B. Saunders Co, Philadelphia, pp 32-33
2. Krantz JC, Carr CJ, LaDu BN 1969 The Pharmacologic Principles of Medical Practice. Williams & Wilkins Co, Baltimore, p 597.
3. Utian WH 1980 Menopause in Moder Perspective: A Guide to Clinical Practice, Appleton-Century-Crofts, New York, pp 151-152.
4. Ryan KJ, Engel LL 1953 The Interconversion of estrone and estradiol by human tissue slices. Endocrinol. 52:287.
5. Yen SSC, Martin PL, Burnier AM, Czekala NM, Greaney MO, Callantine MR 1975 Circulating estradiol, estrone and gonadotropin levels following the administration of orally active 17β-estradiol in postmenopausal women. J Clin Endocrinol Metab 40:518.
6. Stumpf et al 1982, Development of a vaginal ring for achieving physiologic levels of 17β-estradiol in hypoestrogenic women, J Clin Endocrinol Metab, 54:208-210.
7. Englund D. E., 1981, Pharmacokinetics and pharmacodynamic effects of vaginal oestradiol administration from silastic rings in postmenopausal women, Maturitas, 3:125-133.
8. Veldhuls J. et al, 1986, Endocrine impact of pure estradiol replacement in postmenopausal women: Alterations in anterior pituitary hormone release and circulating sex steroid hormone con-
9. Stumpf. P. 1986, Selecting constant serum estra-estradiol levels achieved by vaginal rings, Obstet. Gynecol. 67:91-94, 1986.

We claim:

1. An intravaginal device for use by hypoestrogenic women comprising 17 beta-estradiol incorporated within a supporting elastomeric matrix in such a way that the 17 beta-estradiol will, for at least a month, be continuously released from the elastomeric matrix at an essentially constant rate of about 0.5 to about 25 μg per 24 hours.

2. An intravaginal device according to claim 1 wherein the release rate is from about 1 to about 10 μg/24 h.

3. An intravaginal device according to claim 1 wherein the release rate is from about 4 to about 8 μg/24 h.

4. A method of treating a woman having symptoms of hypoestrogenicity which comprises positioning within the woman an intravaginal device that comprises 17 beta-estradiol incorporated within a supporting elastomeric matrix in such a way that the 17 beta-estradiol will be, for at least a month, continuously released from the elastomeric matrix at an essentially constant rate of about 0.5 to about 25 μg per 24 h.

5. A method according to claim 4 wherein the release rate is from about 1 to about 10 μg/24 h.

6. A method according to claim 4 wherein the release rate is from about 4 to about 8 μg/24 hr.

* * * * *

UNITED STATES PATENT AND TRADEMARK OFFICE
CERTIFICATE OF CORRECTION

PATENT NO. : 5,188,835
DATED : February 23, 1993
INVENTOR(S) : LINDSKOG et al.

It is certified that error appears in the above-indentified patent and that said Letters Patent is hereby corrected as shown below:

On the title page, after item [73], please insert the following:

--[*] Notice: The portion of the term of this patent subsequent to October 3, 2006 has been disclaimed.--

Signed and Sealed this

Sixth Day of August, 1996

Attest:

BRUCE LEHMAN

Attesting Officer

Commissioner of Patents and Trademarks